United States Patent [19]
Afilani

[11] Patent Number: 5,907,280
[45] Date of Patent: May 25, 1999

[54] STATIC ELECTRIFICATION ASSISTED DIELECTROKINESIS DETECTION OF PLASTICS AND OTHER MATERIALS

[75] Inventor: Thomas Afilani, Jersey Shore, Pa.

[73] Assignee: DKL International, Inc., Wilmington, Del.

[21] Appl. No.: 08/846,207

[22] Filed: Apr. 28, 1997

[51] Int. Cl.$^6$ .................................................. G08B 23/00
[52] U.S. Cl. ................................... 340/573.1; 340/568.1; 340/561; 340/562; 324/71.1; 324/72; 324/452; 324/457
[58] Field of Search .................................... 340/573, 572, 340/568, 561, 562, 565, 567, 563, 564, 566, 573.1; 324/71.1, 72, 452, 457

[56] References Cited

U.S. PATENT DOCUMENTS

| | | |
|---|---|---|
| 3,771,152 | 11/1973 | Dettling . |
| 4,040,044 | 8/1977 | Laymon et al. ........................ 340/573 |
| 4,250,415 | 2/1981 | Lewiner et al. ........................ 307/400 |
| 4,339,709 | 7/1982 | Brihier . |
| 4,487,057 | 12/1984 | Lutz ........................................ 73/40.5 |
| 4,553,089 | 11/1985 | Lewiner et al. . |
| 4,992,741 | 2/1991 | Douglas . |
| 5,019,804 | 5/1991 | Fraden . |
| 5,095,278 | 3/1992 | Hendrick . |
| 5,164,673 | 11/1992 | Rosener . |
| 5,184,077 | 2/1993 | Day et al. . |
| 5,315,254 | 5/1994 | Wang et al. . |
| 5,317,252 | 5/1994 | Kranbuehl . |
| 5,432,435 | 7/1995 | Strong et al. . |
| 5,528,133 | 6/1996 | Saklikar . |
| 5,572,115 | 11/1996 | Strong et al. . |

FOREIGN PATENT DOCUMENTS

| | | |
|---|---|---|
| 2413105 | 7/1979 | France . |
| 28 53 075 | 6/1980 | Germany . |
| 2120391 | 11/1983 | United Kingdom . |

OTHER PUBLICATIONS

Hearn, G. L., et al., "The Application of Electrostatics in Forensic Science" Journal of Electrostatics, vol. 23, No. 1 + Index, Apr. 1989, pp. 169–178, XP000004858, see the whole document.

*Primary Examiner*—Nina Tong
*Attorney, Agent, or Firm*—Nixon & Vanderhye P.C.

[57] ABSTRACT

A dielectrokinesis detector includes a chamber housing an exact dielectric replicate reference material that is subjected to external static electrification. The reference material is mechanically constrained, enabling the detection of the polarization energy dynamics of constrained dielectrophoretic force indicating the presence of any target with dielectric properties identical to the properties of the reference material. An antenna assembly increases the proximity distance (range) of detection. The static electrification source for the reference material increases the longevity of the detection ability to provide continuous detection capability, and an external electronic circuit source of electrical energy via an electrical current surge gives a quantifiable manifestation of the detection. In accordance with the principals of dielectrophoresis, the detector can detect the presence of a specific material irrespective of the presence or absence of any type of intervening, visual obstructing material structures, barriers or electromagnetic interference (EMI) signals.

24 Claims, 2 Drawing Sheets

STATIC ELECTRIFICATION ASSISTED DIELECTROKINESIS DETECTION OF PLASTICS AND OTHER MATERIALS

BACKGROUND OF THE INVENTION

This invention relates to the detection of plastics and other materials using dielectrokinesis (phoresis) and, more particularly, to the detection of specific plastics, polymers and other organic and inorganic materials via detection of an electrodynamic reaction current surge to mechanically-constrained, inverse dielectrophoresis force.

Detection of specific polymers and plastics (blends and mixtures of various polymers and with additives) and other organic/inorganic materials, irrespective of the presence of intervening vision-obstructing structures, barriers or EMI signals has uses in very diverse applications such as (a) transportation security in pre-boarding planes, trains and automobiles; (b) new and old construction; (c) law enforcement; (d) military operations; (e) anti-shoplifting protection; and (f) other security needs and operations.

Dielectrophoresis describes the force upon and mechanical behavior of initially charge-neutral matter that is dielectric polarization charged via induction by external spatially non-uniform electric fields. The severity of the spatial non-uniformity of the electric field is measured by the spatial gradient (spatial rate of change) of the electric field. A fundamental operating principle of the dielectrophoresis effect is that the force (or torque) in air or other surrounding media generated at a point and space in time always points (or seeks to point) in the same direction, mainly toward the maximum gradient (non-uniformity) of the local electric field, independent of sign (+ or −) and time variations (DC or AC) of electrical fields (voltages) and of the surrounding medium dielectric properties.

The dielectrophoresis force magnitude depends distinctively nonlinearly upon the dielectric polarizibility of the surrounding medium, the dielectric polarizibility of initially neutral matter and nonlinearly upon the neutral matter's geometry. This dependance is via the Clausius-Mossotti function, well-known from polarizibility studies in solid state physics. The dielectrophoresis force depends nonlinearly upon the local applied electric field produced by the target. The dielectrophoresis force depends upon the spatial gradient of the square (second power) of the target's local electric field distribution at a point in space and time where a detector is located. The spatial gradient of the square of the local electric field is measured by the dielectrophoresis force produced by the induced polarization charge on the detector. This constant-direction-seeking force is highly variable in magnitude both as a function of angular position (at fixed radial distance from the target) and as a function of the radial position (at a fixed angular position) and as a function of the "effective" medium polarizibility. The force's detection signature is a unique pattern of the target's spatial gradient of the local electric field squared, with the detector always pointing (seeking to point) out the direction of the local maximum of the gradient pattern. All experimental results and equations of dielectrophoresis are consistent with the fundamental electromagnetic laws (Maxwell's equations).

There are five known modes of dielectric polarization. These include: electronic polarization, where electron distribution about the atom nuclei is slightly distorted due to the imposed external electric field; atomic polarization, where the atoms' distributions within initially neutral matter are slightly distorted due to the imposed external electric field; nomadic polarization, where in very specific polymers, etc. highly delocalized electron or proton distributions are highly distorted over several molecular repeat units due to the imposed external electric field; rotational polarization (dipolar and orientational), where permanent dipoles ($H_2O$, NO, HF) and orientable pendant polar groups (—OH, —Cl, —CN,— $NO_2$) hung flexibly on molecules in material are rotationally aligned toward the external electric field with characteristic time constants; and interfacial (space charge) polarization, where inhomogeneous dielectric interfaces accumulate charge carriers due to differing small electrical conductivities. With the interfacial polarization, the resulting space charge accumulated to neutralize the interface charges distorts the external electric field with characteristic time constants.

The first three modes of dielectric polarization, electronic, atomic and nomadic, are molecular in distance scale and occur "instantaneously" as soon as the external electric field is imposed and contribute to the dielectric constant of the material at very high frequencies (infrared and optical). The last two polarization modes, rotational and interfacial, are molecular and macroscopic in distance scale and appear dynamically over time with characteristic time constants to help increase the high frequency dielectric constant as it evolves in time toward the dielectric constant at zero frequency. These characteristic material time constants control the dielectric and mechanical response of a material.

The modes of polarization and their dynamics in contributing to the time evolution of dielectric constants are discussed in various publications, such as H. A. Pohl, *Dielectrophoresis,* Cambridge University Press (1978); R. Schiller *Electrons in Dielectric Media,* C. Ferradini, J. Gerin (eds.), CRC Press (1991), and R. Schiller, *Macroscopic Friction and Dielectric Relaxation,* IEEE Transactions on Electrical Insulation, 24, 199 (1989), the well-known teachings of which are hereby incorporated by reference.

If an external electrical field $E_0$ is applied to a dielectric material, the force (F) has a volume density (f=F/v) that includes forces on free charges, bound pairs of charges acting as polarizable dipoles, interactions between the dipoles and dimension changes due to the electric field (E) inside the dielectric material. The general volume force density can be defined in accordance with the following relation:

$$f = F/v = \rho_{charge}E - 1/2(E_0 E)\nabla \epsilon + \\ 1/2\alpha\nabla(E_0 E) + 1/2(\rho_{mass}\partial\epsilon/\partial\rho_{mass})\nabla(E_0 E) \quad (1)$$

$$f = \text{electrostatic force} + \text{dipole} - E_0\text{field force} + \\ \text{dielectrophoresis force} + \text{electrostriction force}$$

where $\epsilon$=dielectric permitivity of the material (which equals $K\epsilon_0$ where K is the dielectric constant of the material and $\epsilon_0$ is the dielectric permitivity of free space), $\alpha$=polarizibility of the dielectric material, $\nabla$=spatial gradient vector mathematical operator, $\partial\epsilon/\partial\rho_{mass}$=partial differentiation mathematical operator, $\rho_{charge}$=volume density of free charges (carriers), and $\rho_{mass}$=volume mass density of the dielectric material.

In the vast majority of dielectrics, $\rho_{charge}=0$ so there is no electrostatic force to be considered. Similarly, with the exception of piezoelectric materials, $\partial\epsilon\partial\rho_{mass}=0$ (i.e., there is no density variation in the dielectric constant), and no electrostriction force has to be considered. The two dielectrokinesis forces, the dipole-$E_0$field force and the dielectrophoresis force, thus remain to be considered.

The first dielectrokinetic force equals zero if the vector gradient of the dielectric permitivity $\epsilon=K\epsilon_0$ is zero (i.e., there is no spatial variation in the effective dielectric constant). If there is some spatial variation in the dielectric constant, then a relatively large force occurs, since the second term in Equation (1) is multiplied by the electric field squared. A simple example of the first dielectrokinesis force is where a warm liquid (having a lower dielectric constant than cold liquid, and therefore a non-zero spatial gradient) is set in motion toward the lower electric field regions. In a complex dielectric body, if $\nabla\epsilon=0$ then all parts of a body are spatially matched dielectrically. The dielectric permitivity $\epsilon$ is a complex material parameter, in particular, for "pure" polymers, as well as "plastics" which are often mixtures or blends of polymers with additives to overcome chemical processing challenges and end-use product functional limitations. See D. W. van Krevelen, *Properties of Polymers and Correlation to Chemical Structure*, Elsevier Press (1976), the teachings of which are hereby incorporated by reference.

The third term in Equation (1), the dielectrophoresis force, enunciated by H. Pohl, involves the spatial gradient of the electric field squared. Hence, this second dielectrokinesis force is smaller than the dipole-dipole dielectrokinesis force.

Therefore, the net force density can be expressed as:

$$f=F/v=-\tfrac{1}{2}(E_0E)\ \nabla\epsilon+\tfrac{1}{2}\ \alpha\nabla(E_0E)$$

$$f=\text{dipole-}E_0\text{force}+\text{dielectrophoresis force} \quad (2)$$

The electrical energy density (U) stored in a dielectric body can be expressed as:

$$F=-\nabla U \quad (3)$$

whereby the energy (U) is the volume integral of the two electrokinesis forces involved.

Therefore, one of two situations, can occur: (1) $\nabla\epsilon$ does not equal zero, and the first dielectrokinesis force in Equation (2) is dominant (i.e., the various parts of the complex dielectric body are not dielectrically spatially matched) and the total energy of the system is large with large variations. This situation denotes "no match detected;" or (2) $\nabla\epsilon$ equals zero, and the dielectrophoresis (Pohl) force in Equation (2) is dominant (i.e., the various parts of the complex dielectric body are dielectrically spatially matched) and the total energy of the system is small with small variations. This situation denotes "match detected."

In situation 2 (match detected), force density (f) is expressed as:

$$f=F/v=\tfrac{1}{2}\ G\ \nabla|K_1\epsilon_0E_0E_0| \quad (4)$$

$$f=F/v=\tfrac{1}{2}\ G\ \nabla|2U_0| \quad (5)$$

where $E=G\ E_0$ converts the electrical field in dielectric (E) to external field ($E_0$), $G=3\ (K_2-K_1)/(K_2+2K_1)$ for spherically shaped dielectric objects and $G=2\ (K_2-K_1)/(K_2+K_1)$ for cylindrically shaped dielectric objects (with $K_2$ being the dielectric constant of the material in the sphere or cylinder that is dielectrically spatially matched to a reference sample, and with $K_1$ being the dielectric constant of the surrounding fluid (gas or liquid)), and $U_0$ the electrical energy density "stored" in the external electric field $E_0$.

It would be advantageous utilizing the concepts noted above to enable the detection of polymers and plastics and other organic/inorganic materials irrespective of the presence of intervening vision obstructing structures, barriers or EMI signals.

SUMMARY OF THE INVENTION

Such an application has been achieved in accordance with the present invention. The invention relates to a detector using novel combinations of initially neutral matter objects, which has allowed for the detection of hidden specific polymers and plastics with a high degree of discrimination even between nominally identical plastics formulations where the only difference is the presence or absence of certain additives.

The observation of a dielectrophoresis force effect is usually through a torque-type "action at a distance" and the manifestation of dielectrophoresis forces acting at variable, yet integratable, distances from a well-defined pivot point and line as is described in commonly owned, co-pending patent application Ser. No. 08/758,248, the disclosure of which is hereby incorporated by reference. In the present invention, a different technical strategy is employed wherein the initial neutral matter object is the entity target to be detected, whereas in the co-pending application, the initial neutral matter object is the central detection medium itself. In this case, a material source object with identical chemical and dielectric properties to those of the initially neutral matter "target" material object is used as the detection medium.

The external electric field and the spatial gradients thereof are produced by continual static electrification of the detection reference medium itself. This spatial gradient of the detection medium's external electric field produces a dielectrophoresis force on any identical, initially neutral target material object coming within the proximity (range) of the detection medium. Both the chemically and dielectrically identical target and detection medium are mechanically constrained so as to not be able to move in response to the dielectrokinetic forces present. Consequently, they cannot mechanically dissipate energy, and a current surge is generated.

As the identical target material of interest comes within the proximity (range) of the detector medium, the external electric field produced by the continual static electrification produces an induced polarization pattern in an initially neutral identical target material, which takes energy from $U_0$, the energy density stored in the external electric field.

The manifestation detection signal used to indicate the presence of the specific type of plastic, polymer or other organic/inorganic material is an electric energy surge in the form of a current surge from an electromotive energy source (battery) attached to the detection medium via an electronic circuit. With a detection device incorporating the structural concepts according to the invention, plastics and other entities can be detected irrespective of the presence of any intervening, vision-obstructing structures or barriers (suitcases, walls etc.) or electromagnetic interference (EMI) signals. All other (non-matching) plastics and other materials do not give an energy surge because the forces and associated energy is much larger than can be supplied by the electronic circuit attached to a reference dielectric material located within the detection device.

BRIEF DESCRIPTION OF THE DRAWINGS

Further objects and advantages of the present invention will be described in detail with reference to the accompanying drawings, in which.

DETAILED DESCRIPTION OF PREFERRED EMBODIMENTS

Figure 1:
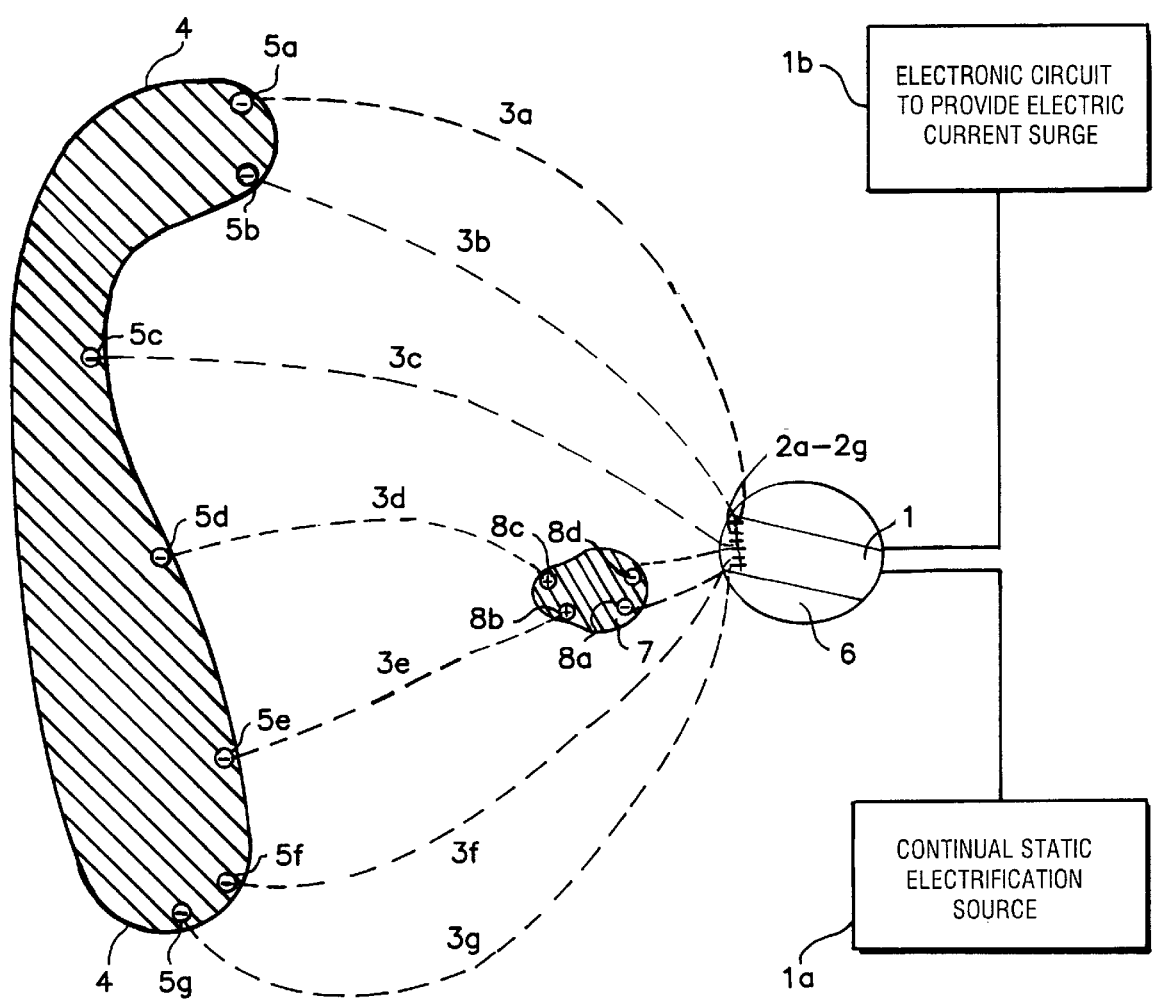
FIG. 1 is a schematic drawing of the detection medium position, its electric field lines, the position of the identical target material of interest and its induced polarization pattern.

The FIG. 1 illustration schematically shows the position of the reference material entity 1 having a source of continual static electrification 1a and an electronic circuit 1b to provide an electric current surge. The static electrification source 1a induces static charges 2a–2g on the reference material, which is mechanically constrained in cavity 6, to produce a non-uniform electric field, illustrated by lines 3a–3g. The field lines have a unique spatial pattern as well as a unique spatial gradient pattern. The reference material electric field terminates on the surrounding ground plane 4, thereby inducing opposite charges 5a–5g on a surface of the ground plane 4.

Conceptually, when an initially neutral entity of a target dielectric material 7 passes into the environment of electric field lines 3a–3g and spatial gradients, polarization charges 8a–8d are induced on the target material 7. If the dielectric properties of the target material 7 are identical to those of the reference material 1, only the dielectrophoresis force manifests itself in accordance with the dielectrophoresis phenomena discussed above. Because the target material 7 and reference material 1 are mechanically constrained (described below), they do not respond to the dielectrophoresis force, and the electronic circuit 1b provides a quantifiable current surge in response to the creation of the polarization charges 8a–8d.

Figure 2:
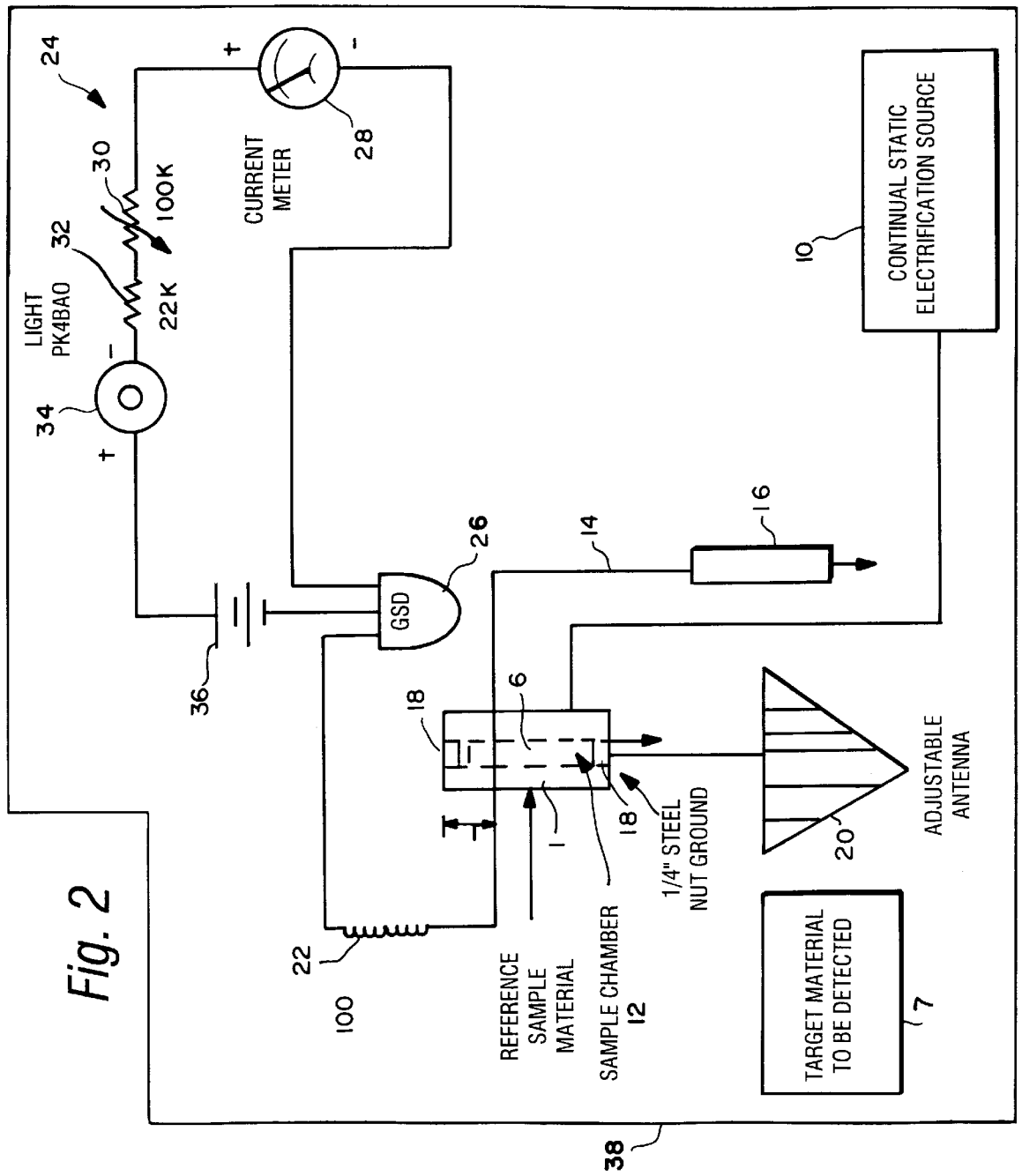
FIG. 2 is a schematic drawing of a prototype electronic circuit attached to the detection medium.

FIG. 2 is a detailed schematic of the detector according to the present invention including electronic circuit 1b from FIG. 1. A reference material chamber 12 mechanically constrains the reference material. Examples of suitable reference materials include PVC, ABS, and others. A grounding wire 14 runs through the reference material to a grounding steel rod 16. The reference material chamber 12 is closed with a pair of conducting end inserts 18 such as steel nuts at opposite ends of the chamber. In an alternative configuration, the grounding wire 14 is coupled directly with one of the conducting end inserts 18. An adjustable antenna 20 is coupled with one of the conducting end inserts 18 and may have a common ground with the steel rod 16. The antenna 20 serves to increase the proximity distance (range) of the detector.

The grounding wire 14 is connected in series to the material, which connects in series to a copper wire inductor choke 22 such as a 100-turn copper wire inductor. The choke then connects in series to the gate input of a field effect transistor 26, such as a NTE 312 FET. The field effect transistor 26 closes a detector circuit 24 under the control of the signal provided to the gate input via the choke 22. The circuit 24 includes, in a series connection, a current meter 28, a variable 100K Ω resistor 30, a fixed 22K Ω resistor 32, a current indicator light 34, and a battery 36, such as a 9-volt battery. Of course, different resistive values can be selected in accordance with the power supply 36, the meter 28 characteristics, etc. When the detector circuit 24 is closed by the transistor 26, the battery 36 appears across the load 30/32 and light 34. The detector circuit 24 provides a discernable indication of current in the line 14, which in turn is an indication of the presence of the target material 7. As an alternative, the detector circuit may be provided by an amplifier and current meter connected in series with the choke 22.

The components of the detector can be suitably arranged within a portable self-contained casing 38.

In operation, the continual static electrification source 10 keeps the reference material sample charged on its outside surface, providing an external electric field and its spatial gradients. When the target material to be detected 7, matching the dielectric properties of the reference material 1, is caused to enter the electric field and its spatial gradients provided by the reference material 1, energy is withdrawn from the external electric field in accordance with the general volume force-density concepts discussed above, generating a current surge along line 14. The small current is sufficient to cause the field-effect transistor 26 to close the detector circuit 24, thereby generating a current pulse through the current meter 28 and the indicator light 34 by virtue of the battery 36. The light 34 and meter 28 thus become an indicator of the current surges on line 14, and thus an indicator of the presence of the target material.

In accordance with the present invention, an external electric field and spatial gradients thereof can be produced by a source of continual static electrification of a detection reference medium. The spatial gradients produce a dielectrophoresis force on any identical, initially neutral target material object coming within proximity distance (range) of the detection medium. Because the reference material and the target material are mechanically constrained, the dielectrophoresis force manifests a current surge sufficient to activate a detector circuit, providing a current surge to a current meter and/or an indicator light.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims. For example, in one alternative configuration, the reference material chamber 12 can be replaced with a reference component chamber sized to interchangeably receive independent reference components that mechanically constrain different reference materials, respectively. In this context, an operator can readily change the reference material in accordance with various desired target materials.

What is claimed is:

1. A dielectrokinesis detector for detecting the presence or absence of a target material, the detector comprising:

a detector housing having a reference material chamber;

a reference material disposed in said chamber, said reference material being selected in accordance with dielectric characteristics of the target material;

a source of static electrification disposed in said detector housing, said static electrification source being directed at said reference material to thereby induce a static charge on said reference material; and a detection circuit disposed in said housing, said detection circuit being activated in accordance with the presence of the target material.

2. A dielectrokinesis detector according to claim 1, further comprising a ground lead disposed in electrical communication with said reference material, said ground lead in one direction being coupled to ground and in an opposite direction being coupled to a switch that serves to close said detection circuit in accordance with a current in said ground lead.

3. A dielectrokinesis detector according to claim 2, wherein the switch is a field effect transistor.

4. A dielectrokinesis detector according to claim 2, further comprising an inductor choke in series with said ground lead between said reference material and said switch.

5. A dielectrokinesis detector according to claim 2, wherein said reference material chamber is capped at its ends with a pair of conducting end inserts, said end inserts and said chamber mechanically constraining said reference material, said ground lead being electrically connected to one of said end inserts.

6. A dielectrokinesis detector according to claim 1, wherein said detection circuit comprises, in series, a current meter, a load and a battery.

7. A dielectrokinesis detector according to claim 6, wherein said detection circuit further comprises an indicator light disposed in series with said load and said battery, and wherein said load comprises a variable resistor and a fixed resistor.

8. A dielectrokinesis detector according to claim 1, wherein said reference material chamber is capped at its ends with a pair of conducting end inserts, said end inserts and said chamber mechanically constraining said reference material.

9. A dielectrokinesis detector according to claim 8, further comprising an antenna electrically connecting one of said conducting end inserts.

10. A detector for detecting the presence or absence of a non-conducting target material, the detector comprising:
    a reference material chamber mechanically constraining a reference material, said reference material being selected in accordance with dielectric characteristics of the target material;
    a source of static electrification directed at said reference material to thereby induce a static charge on said reference material; and
    a detection circuit disposed in said housing, said detection circuit being activated in accordance with the presence of the target material.

11. A detector according to claim 10, further comprising a ground lead disposed in cooperation with said reference material, said ground lead in one direction being coupled to ground and in an opposite direction being coupled to a switch that serves to close said detection circuit in accordance with a current in said ground lead, said current being generated in accordance with a manifested dielectrophoresis force by virtue of a non-uniform electric field having a unique spatial pattern and a unique spatial gradient pattern generated by the static charge on said reference material.

12. A detector according to claim 11, wherein the switch is a field effect transistor.

13. A detector according to claim 11, further comprising an inductor choke in series with said ground lead between said reference material and said switch.

14. A detector according to claim 11, wherein said reference material chamber is capped at its ends with a pair of conducting end inserts, said end inserts and said chamber mechanically constraining said reference material, said ground line being electrically connected to one of said end inserts.

15. A detector according to claim 10, wherein said detection circuit comprises, in series, a current meter, a load and a battery.

16. A detector according to claim 15, wherein said detection circuit further comprises an indicator light disposed in series with said load and said battery, and wherein said load comprises a variable resistor and a fixed resistor.

17. A detector according to claim 10, wherein said reference material chamber is capped at its ends with a pair of conducting end inserts, said end inserts and said chamber mechanically constraining said reference material.

18. A detector according to claim 17, further comprising an antenna electrically connected to one of said conducting end inserts.

19. A method of detecting the presence or absence of a target material with a detector including a reference material chamber containing a reference material, a source of static electrification directed at the reference material, and a detection circuit, the method comprising:
    (a) mechanically constraining the reference material contained in the reference material chamber;
    (b) inducing a static charge on the reference material with the static electrification source; and
    (c) activating the detection circuit in accordance with the presence of the target material.

20. A method according to claim 19, wherein step (c) is practiced in accordance with a manifested dielectrophoresis force by virtue of a non-uniform electric field having a unique spatial pattern and a unique spatial gradient pattern generated by the static charge on the reference material.

21. A method according to claim 19, further comprising, prior to step (a), the step of selecting the reference material in accordance with dielectric characteristics of the target material.

22. A dielectrokinesis detector for detecting the presence or absence of a target material, the detector comprising:
    a detector housing having a reference material component chamber for housing a reference material component;
    a source of static electrification disposed in said detector housing, said static electrification source being directed at said reference material component chamber to thereby induce a static charge on the reference material component; and
    a detection circuit disposed in said housing, said detection circuit being activated in accordance with the presence of the target material.

23. A dielectrokinesis detector according to claim 22, further comprising a reference material component disposable in said reference material component chamber, said reference material component containing the reference material, wherein the reference material is selected in accordance with dielectric characteristics of the target material.

24. A dielectrokinesis detector according to claim 22, further comprising a plurality of reference material components interchangeably disposable in said reference material component chamber, said reference material components each containing a different reference material, wherein the reference material is selected in accordance with dielectric characteristics of the target material.

* * * * *